United States Patent [19]
Piazza et al.

[11] 4,230,111
[45] Oct. 28, 1980

[54] HYGIENIC SYRINGE AND CLEANSING METHOD

[76] Inventors: Nicholas F. Piazza; Joan A. Piazza, both of 13 Alpine Way, Huntington Station, N.Y. 11746

[21] Appl. No.: 29,728

[22] Filed: Apr. 13, 1979

[51] Int. Cl.³ .............................................. A61M 3/00
[52] U.S. Cl. .................................... 128/225; 128/251
[58] Field of Search ............... 128/225, 224, 232, 260, 128/251, 272, 261

[56] References Cited

U.S. PATENT DOCUMENTS

| | | | |
|---|---|---|---|
| 94,029 | 8/1869 | Puffer | 128/227 |
| 1,719,163 | 7/1929 | Bergl | 128/225 X |
| 1,892,750 | 1/1933 | Rotheim | 128/225 X |
| 2,806,238 | 9/1957 | Wisey, Jr. | 128/225 X |
| 3,162,194 | 12/1964 | Indelicato | 128/261 |
| 3,275,000 | 9/1966 | Bowen | 128/225 X |
| 4,112,942 | 9/1978 | Scaife | 128/225 |

FOREIGN PATENT DOCUMENTS 640633  7/1928  France ..................... 128/225

*Primary Examiner*—John D. Yasko
*Attorney, Agent, or Firm*—Philip H. Gottfried

[57] ABSTRACT

A syringe and method for use in propelling an effervescing liquid mixture for purposes of hygienic irrigation. A pre-charged liquid mixture is stored in a container having a sealable cap. When the container is shaken, gas is released from the mixture so as to pressurize the container. The mixture can then be propelled in an effervescing state to a fountain nozzle when the container cap is moved to release the cap seal.

11 Claims, 4 Drawing Figures

HYGIENIC SYRINGE AND CLEANSING METHOD

DESCRIPTION OF THE INVENTION

The present invention relates generally to hygienic syringes, and more particularly to a syringe and method for providing a self-propelled, effervescing liquid mixture for purposes of hygienic irrigation.

Hygienic syringes or dispensers for propelling a liquid mixture such as a douche or enema solution out through a fountain nozzle are known in the art, examples appearing in U.S. Pat. Nos. 2,716,984 and 3,354,883.

The dispenser of the '984 patent includes a cylindrical reservoir for containing a liquid mixture, and a cover which threadably engages the container. The cover includes a fountain nozzle and a control valve assembly, the latter being actuable by a hand lever. The cover also supports a dry, gas-forming tablet above the liquid contents of the container so that, when shaken, the tablet dissolves in the liquid and gas is released to pressurize the container. When the hand lever is squeezed, the liquid contents are then expelled through the nozzle.

In the syringe of the '883 patent, a dry medicament is supported above liquid contained in a squeeze bulb container. When ready for use, a fountain nozzle extending from the container cap is pressed down to cause the dry medicament to drop into the liquid and dissolve. The liquid mixture which may then be effervescing is expelled from the nozzle by squeezing the bulb.

It will be appreciated, however, that the prior dispensers or syringes in which a dry tablet or powder is mixed with a contained liquid just prior to use suffer from the disadvantage that the dry substance may inadvertently be caused to mix with the liquid contents well before the dispenser is ready to be used. Shortly thereafter, any pressure developed within the dispenser or any effervescence provided to the liquid mixture will subside and thereby necessitate the replacement of the liquid and the insertion of a new tablet or powder before the dispenser can be used.

U.S. Pat. No. 94,029 shows a syringe including a corked vessel containing carbonate of liquid. When ready to be used, a champagne faucet having a valve cock therein is screwed into the cork. Turning the valve then allows the liquid contents to be emptied from the vessel through the faucet. Such an arrangement, however, requires that the user already possess or separately purchase the faucet mechanism which is not an integral part of the corked vessel. Also, as often occurs when one inserts a corkscrew into a bottle cork, pieces of the cork break away and a sufficient liquid seal between the cork, the vessel and the faucet may not be maintained so as to impair effective use of such a syringe arrangement.

It is an object of the present invention to overcome the above and other shortcomings in the prior hygienic dispensers and syringes.

It is another object of the present invention to provide a hygienic syringe which is capable of propelling an effervescing liquid mixture without the use of dry tablets or powders.

It is yet another object of the present invention to provide a hygienic syringe of relatively simple construction and which can be readily put to use.

It is a still further object of the present invention to provide a hygienic syringe which easily lends itself to various hygienic irrigation applications.

In accordance with the present invention, a hygienic syringe for dispensing an effervescing liquid mixture comprises a container for storing a liquid mixture, the container having a neck portion extending therefrom. A cap is provided for movably engaging the neck portion, the cap having an opening to communicate the liquid mixture in the container to a fountain nozzle. Sealing means is provided on the container neck portion, and is responsive to movement of the cap so as to prevent the liquid mixture from entering the cap opening when the cap is in a first position, and for enabling the liquid mixture to pass through the cap opening when the cap is in a second position. The liquid mixture has a gas dissolved therein when stored in the container and the cap is in the first position. When the gas is released from the liquid mixture, and the cap is moved to a second position, the liquid mixture is propelled out of the container in an effervescing state through the cap opening in response to pressure developed by the released gas.

A method for dispensing an effervescing liquid mixture, in accordance with the present invention, comprises the steps of providing a liquid mixture with a predetermined quantity of dissolved gas, and thereafter placing the mixture inside of a container which is then sealed with a movable cap. The method also includes the steps of shaking the container so that a portion of the dissolved gas is released from the liquid mixture, and propelling the liquid mixture out of the container in an effervescing state in response to pressure developed by the released gas within the container.

The above brief description, as well as further objects, features and advantages of the present invention will be more fully understood by reference to the following detailed description of the presently preferred, but nonetheless illustrative embodiment, in accordance with the present invention, when taken in conjunction with the accompanying drawing, wherein.

Figure 3:
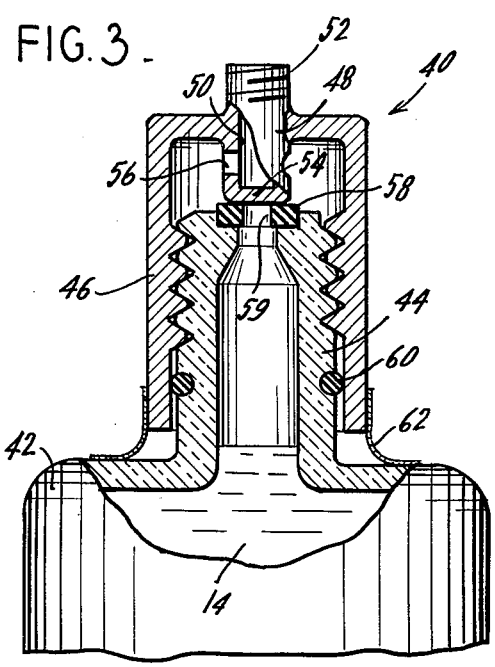
Figure 4:
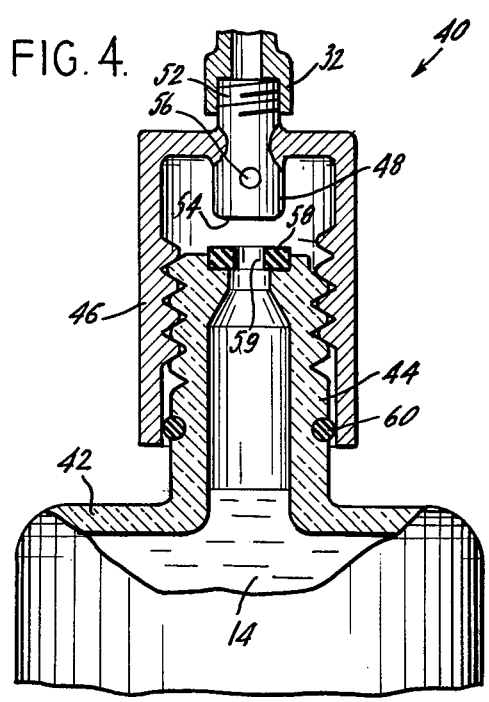

FIG. 3 is a fragmentary front elevational view, partly in cross-section, of a second embodiment of a hygienic syringe showing a container having a neck portion, and a sealed container cap in accordance with the present invention; and FIG. 4 is a fragmentary front elevational view of the hygienic syringe of FIG. 3 showing a fountain nozzle threaded onto the container cap and showing the cap moved to a position whereat the container seal is opened.

Figure 1:
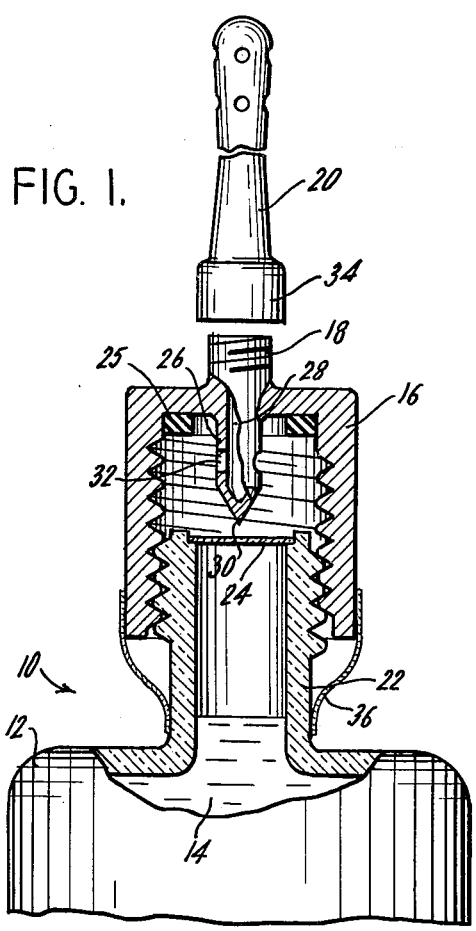
FIG. 1 is a fragmentary front elevational view, partly in cross-section, of a hygienic syringe showing a container having a neck portion, a container cap and a fountain nozzle, in accordance with the present invention.

Referring now in detail to the drawing, and initially to FIG. 1 thereof, in accordance with an illustrative embodiment demonstrating objects and features of the present invention, there is provided a hygienic syringe generally designated by the reference numeral 10. Basically, the syringe 10 includes a rigid or at least semi-rigid container 12 which may be of glass, plastic or other like sturdy material which is capable of maintaining a liquid mixture 14 therein without deforming or breaking during the course of transport or handling thereof. Container 12 should also be capable of withstanding a relatively moderate internal positive pressure without appreciably deforming, as will be better understood by the description which follows. Syringe 10 also includes a sealable cap 16 for the container 12, cap 16 being provided with a coupling 18 for engaging a fountain nozzle 20.

In further detail, container 12 has a neck portion 22 across the top of which is provided a membrane seal 24. Seal 24 is tightly bonded about its periphery to the neck portion 22 and can be made of one of a number of conventional materials which can be relatively easily punctured when the seal is to be broken, and yet prevent the liquid mixture 14 from leaving the container 12 before the syringe 10 is to be used. Examples of suitable materials for the seal 18 include any of the natural and synthetic rubbers, elastomers and non-corrosive metal foils.

The container cap 16 is internally threaded, as shown, so as to mate with corresponding external threads on the container neck portion 22. A ring gasket 25 is seated against the interior walls of the cap 16 for sealing against the top edge of the container neck portion 22, as will be explained hereinafter in connection with FIG. 2. A conduit 26 projects downwardly within the cap 16, the conduit 26 having an opening 28 extending axially therethrough. Also, conduit 26 is tapered as at 30 to provide a point suitably sharp to puncture the seal 24. Opening 28 thus extends between the tapered point at 30 and the top of the threaded coupling 18 on cap 16. One or more apertures 32 extend radially through the conduit 26 in the vicinity of its point 30.

Nozzle 20 has threads (not shown) within its base 34, which threads will engage the threads provided on the coupling 18 in the event it is desired to place the nozzle 20 directly on the cap 16. Should it be desired to maintain the syringe container 12 remote from the location where the nozzle 20 is to be placed, a flexible tube (not shown) of conventional design, having threaded couplings at its respective ends, can be used to connect the cap 16 with the nozzle 20 for conducting the liquid mixture 14 therethrough.

In order to prevent inadvertent rotation of the cap 16 before the syringe 10 is put to use, a conventional sealing tape 36 is tightly secured about at least the lower portion of the cap 16 and the container 12. Tape 36 may be of rubber, plastic, metal foil or like sheet material which can be torn free without difficulty prior to use of the syringe 10.

The liquid mixture 14 within container 12 may, for example, include a conventional man-made or naturally-occurring hygienic liquid formulation such as plain carbonated water or one of the many readily available feminine douche mixtures or combinations thereof. Such formulations include but are not limited to those marketed under the trademarks "Massengill" by Beecham Inc., Clifton, N.J. "Summer's Eve" by C. B. Fleet Co., Inc., Lynchburg, Va. and "Feminique" by Ennis Laboratories, Ltd., Edison, N.J. Also, plain club soda or plain white vinegar can be used. In accordance with the present invention, approximately one part of any of the above liquid douche formulations is then combined with three parts of a conventional, commercially obtainable carbonated or seltzer water.

Figure 2:
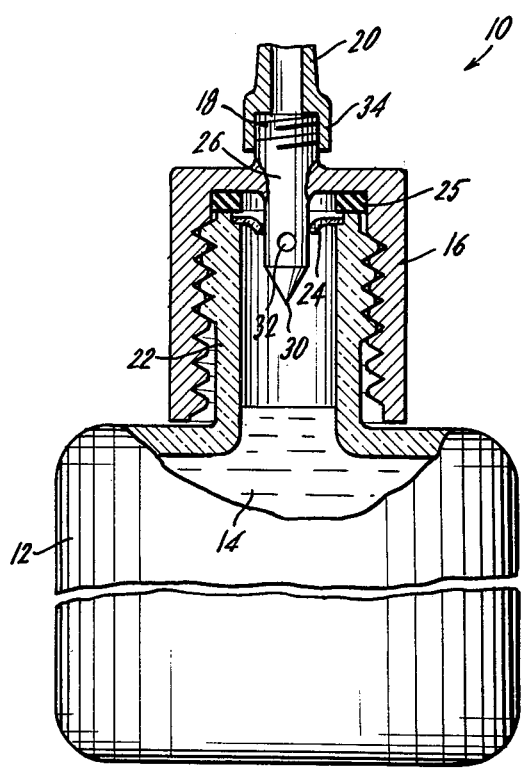
FIG. 2 is a fragmentary front elevational view of the hygienic syringe of FIG. 1, showing the container cap moved to a position whereat a container seal is opened.

Referring now to FIG. 2, operation of the syringe 10 will now be explained.

Container 12 is first shaken vigorously so as to cause some of the gas dissolved in the carbonated water within the mixture 14 to be released therefrom and to develop a positive pressure within the container 12. As the gases are released, it will be appreciated that the entire mixture 14 will be brought into an effervescing state. The container is then inverted, and cap 16 is rotated after the tape 36 is removed so as to cause the conduit 26 to move axially downwardly and puncture the membrane seal 24, as shown in FIG. 2. Cap 16 is also rotated sufficiently far down so that the gasket element 25 therein is compressed between the upper interior region of the cap 16 and the top of the neck portion 22 to prevent leakage of air or liquid therebetween.

It will be appreciated that the axial opening 28 extending within the conduit 26 now communicates with the interior of the container 12 by way of the apertures 32 in the vicinity of the tapered conduit point 30. Therefore, the effervescing liquid mixture 14 will be propelled through the opening 28 and out from the nozzle 20 in response to the pressure developed within the container 12 by the released gas.

Referring now to FIGS. 3 and 4, a second embodiment of a hygienic syringe in accordance with the present invention is designated generally by the reference numeral 40. The syringe 40 basically includes a container 42 having a neck portion 44 extending upwardly therefrom, and a container cap 46 which is threaded internally to mate with corresponding threads on the container neck portion 44, as shown. The cap 46 has a conduit 48 projecting downwardly therein, the conduit 48 including an axial opening 50 therein which extends through a threaded coupling 52 formed at the top of the cap 46. The bottom end of the conduit 48 is closed to provide a substantially flat end wall at 54. Conduit 48 also includes one or more apertures 56 extending radially therethrough to communicate with the opening 50.

A washer 58 defining an outlet opening 59 is seated about the edge of the top opening of neck portion 44 so that, when the end wall 54 of the conduit 48 is compressed against the washer, a seal is formed to prevent liquid contents 14 in the container 42 from being expelled through the outlet opening 59. Further, an O-ring 60 is seated within a circumferential groove formed about the base of the neck portion 44, the O-ring forming a seal between the neck portion 44 and the interior region of the cap 46.

In order to prevent inadvertent rotation of the cap 46 prior to making use of the syringe 40, a sealing tape 62 of rubber, plastic, metal foil or like sheet material is tightly secured against the lower portion of the cap 46 and the upper portion of the container 42, as shown in FIG. 3.

Referring now to FIG. 4, syringe 40 is put to use by vigorously shaking the container 42 so that the liquid mixture 14 will release gas and begin to effervesce. Container 42 is then inverted and, after tape 62 is removed, cap 46 is rotated so that it moves axially upwardly to open the seal between the conduit end wall 54 and the washer 58. The mixture 14 will then be propelled into the interior region of the cap 46, through the conduit apertures 56 and out through the opening 50 extending up through the cap coupling 52. As shown partially in FIG. 4, the fountain nozzle 32 is directly threaded onto the coupling 52 but, as with the embodiment of FIGS. 1 and 2, a flexible tube having threaded couplings at its ends for mating with the cap coupling 52 and nozzle 32, respectively, can also be provided if the nozzle 32 is to be located remote from the syringe 40.

The hygienic syringe of the present invention is of relatively simple construction, thus enabling it to be produced at low cost and with fairly inexpensive materials. Importantly, no dry tablets or powders need be added to its contents prior to use, and syringes according to the present invention can be stored for relatively long periods of time without losing their effectiveness.

As will be readily apparent to those skilled in the art, the present invention may be realized in other specific forms without departing from its spirit or essential characteristics. For instance, although the examples given above for the liquid mixture 14 are for purposes of feminine hygiene, an enema solution including a sufficient amount of dissolved gas may be used as well to provide a self-propelled, effervescing enema wash liquid.

The present embodiments are, therefore, to be considered as illustrative and not restrictive, the scope of the invention being indicated by the claims rather than by the foregoing description, and all changes which come within the meaning and range of equivalents of the claims are intended to be embraced therein.

What is claimed is:

1. A hygienic syringe for dispensing a hygienic liquid mixture in an effervescing state comprising a container having a neck portion extending therefrom, a hygienic liquid mixture within said container having a gas dissolved therein when said hygienic liquid mixture is stored within said container in a pre-charged condition, said hygienic liquid mixture reaching an effervescing state when said dissolved gas is released therefrom by sufficient disturbance of said precharged condition of said hygienic liquid mixture within said container, a cap constructed and arranged to movably engage said neck portion and having a cap opening therein to communicate the hygienic liquid mixture in said container to a dispensing location, and sealing means on said neck portion and responsive to movement of said cap for preventing said hygienic liquid mixture in said precharged condition from entering said cap opening when said cap is in a first position and for enabling said hygienic liquid mixture when in said effervescing state to be propelled out of said container through said cap opening in response to pressure developed within said container by said released gases when said cap is in a second position.

2. A hygienic syringe according to claim 1, wherein said sealing means comprises a washer mounted on said neck portion so as to define an outlet opening for passage of said liquid mixture from said container, said cap being constructed and arranged to movably engage said neck portion and including a conduit projecting downwardly therein, said conduit having said cap opening extending therein from the outside of said cap and terminating at an end wall at the bottom of said conduit, said end wall sealingly engaging said outlet opening in said neck portion when said cap is in said first position, said conduit also having at least one aperture extending therethrough in the vicinity of said end wall for communicating said hygienic liquid mixture from said outlet opening to said cap opening when said cap is in said second position.

3. A hygienic syringe according to claim 1, wherein said liquid mixture includes carbonated water.

4. A hygienic syringe according to claim 1, wherein said liquid mixture comprises about one part of a liquid feminine douche formulation and about three parts of carbonated water.

5. A hygienic syringe according to claim 1, wherein said cap has a coupling thereon, said cap opening extending through said coupling, and further including a fountain nozzle constructed and arranged to be in communication with said cap opening.

6. A hygienic syringe according to claim 5, wherein said fountain nozzle has a base for directing engaging said coupling.

7. A hygienic syringe according to claim 1, further including restraining means for maintaining said cap stationary with respect to said container neck portion so that said cap remains in said first position until moved by a user to said second position.

8. A hygienic syringe according to claim 7, wherein said restraining means is in the form of a removable tape which overlies at least a portion of said cap and said container, respectively.

9. A sealable cap for dispensing liquid contents within a container having a neck portion extending therefrom, said neck portion having an outlet opening for passage of said liquid contents at one end thereof, said cap being constructed and arranged to movably engage said neck portion and including a conduit projecting downwardly therein, said conduit having an opening extending therein from the outside of said cap and terminating adjacent said outlet opening at an end wall at the bottom of said conduit, said end wall sealingly engaging said outlet opening in said neck portion when said cap is in a first position relative to said neck portion, said conduit also having at least one aperture extending therethrough in the vicinity of said end wall for communicating said liquid contents from said outlet opening to said conduit opening when said cap is in a second position relative to said neck portion.

10. A sealable cap as defined in claim 9, wherein said cap and said conduit are constructed and arranged so that said end wall is displaced from said outlet opening when said cap is in said second position, the interior region of said cap being adapted to conduct said liquid contents from said outlet opening to said aperture in said conduit.

11. A method for dispensing a hygienic liquid mixture in an effervescing state to cleanse a predetermined body area comprising the steps of forming a hygienic liquid mixture in a pre-charged condition by placing a hygienic liquid inside of a container and dissolving a predetermined quantity of gas therein, sealing said container while retaining said hygienic liquid and said gas dissolved therein in said pre-charged condition, thereafter shaking said container to sufficiently disturb said pre-charged condition such that a portion of said dissolved gas is released therefrom to develop a sufficient pressure within said container to provide said hygienic liquid mixture in an effervescing state, promptly opening said container proximate said predetermined body area, thereby propelling said hygienic liquid mixture through said opening and out of said container in said effervescing state in response to the pressure developed by said released gas, to cleanse said predetermined body area.

* * * * *